United States Patent
Castellin et al.

(10) Patent No.: US 6,855,834 B2
(45) Date of Patent: Feb. 15, 2005

(54) PROCESS FOR THE PREPARATION OF PURE CITALOPRAM

(75) Inventors: Andrea Castellin, Mestrino (IT); Giulio Volpe, Padua (IT); Federico Sbrogiò, Favaro Veneto (IT)

(73) Assignee: H. Lundbeck A/S, Valby-Copenhagen (DE)

( * ) Notice: Subject to any disclaimer, the term of this patent is extended or adjusted under 35 U.S.C. 154(b) by 0 days.

(21) Appl. No.: 10/035,005

(22) Filed: Dec. 20, 2001

(65) Prior Publication Data

US 2002/0087012 A1 Jul. 4, 2002

Related U.S. Application Data

(63) Continuation of application No. PCT/DK01/00148, filed on Mar. 7, 2001.

(30) Foreign Application Priority Data

Dec. 28, 2000 (DK) .................................. 2000 01943

(51) Int. Cl.$^7$ .................................. C07D 307/87
(52) U.S. Cl. .................................. 549/467
(58) Field of Search .................................. 549/467

(56) References Cited

U.S. PATENT DOCUMENTS

| | | | |
|---|---|---|---|
| 3,449,220 A | 6/1969 | Geisler et al. | |
| 3,467,675 A | 9/1969 | Petersen et al. | 260/346.2 |
| 3,855,080 A | 12/1974 | Becker et al. | 203/89 |
| 4,009,152 A | 2/1977 | Mormann et al. | |
| 4,136,193 A | 1/1979 | Bogeso et al. | 424/285 |
| 4,650,884 A | 3/1987 | Bogeso | 549/467 |
| 4,943,590 A | 7/1990 | Boegesoe et al. | 415/469 |
| 5,207,874 A | 5/1993 | Hess et al. | 206/8 |
| 5,296,507 A | 3/1994 | Tanaka et al. | 514/465 |
| 5,582,692 A | 12/1996 | Baird | 203/49 |
| 5,880,297 A | 3/1999 | Ryan et al. | 549/541 |
| 6,020,501 A | 2/2000 | Massonne et al. | 549/307 |
| 6,028,204 A | 2/2000 | Massonne et al. | 549/307 |
| 6,229,026 B1 | 5/2001 | Petersen | 549/467 |
| 6,258,842 B1 | 7/2001 | Petersen et al. | 514/469 |
| 6,291,689 B1 | 9/2001 | Petersen et al. | 549/467 |
| 6,334,935 B1 | 1/2002 | Uehara et al. | |
| 6,419,797 B1 | 7/2002 | Scherf et al. | |
| 6,455,710 B1 | 9/2002 | Villa et al. | |

FOREIGN PATENT DOCUMENTS

| | | | |
|---|---|---|---|
| EP | 1 095 926 | 5/2001 | C07C/33/46 |
| GB | 2072025 A | 9/1981 | |
| JP | 60082101 | 5/1985 | |
| WO | 98/19511 | 5/1998 | |
| WO | 98/19512 | 5/1998 | |
| WO | 98/19513 | 5/1998 | |
| WO | 99/30548 | 6/1999 | |
| WO | 00/11926 | 3/2000 | |
| WO | 00/12044 | 3/2000 | |
| WO | 00/13648 | 3/2000 | |
| WO | 00/23431 | 4/2000 | C07D/307/87 |
| WO | 00/39112 | 7/2000 | C07D/307/87 |
| WO | 00/44738 | 8/2000 | C07D/307/88 |
| WO | 01/45483 | 6/2001 | |
| WO | 01/47877 | 7/2001 | |
| WO | 01/66536 | 9/2001 | C07D/307/87 |

OTHER PUBLICATIONS

U.S. Appl. No. 09/794,762, filed Feb. 26, 2001.
U.S. Appl. No. 09/794,755, filed Feb. 26, 2001.
U.S. Appl. No. 09/830,109, filed Oct. 19, 1999 (International filing date).
U.S. Appl. No. 09/888,067, filed Jun. 22, 2001.
U.S. Appl. No. 09/891,874, filed Jun. 25, 2001.
U.S. Appl. No. 09/917,180, filed Jul. 27, 2001.
U.S. Appl. No. 09/692,653, filed Oct. 19, 2000.
U.S. Appl. No. 09/930,110, filed Aug. 14, 2001.
U.S. Appl. No. 09/977,920, filed Oct. 15, 2001.

(List continued on next page.)

*Primary Examiner*—Bernard Dentz
(74) *Attorney, Agent, or Firm*—Darby & Darby

(57) ABSTRACT

A process for the preparation of citalopram of formula (I)

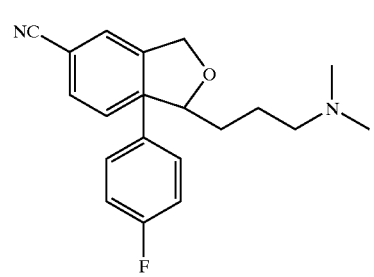

in which a compound of formula (II)

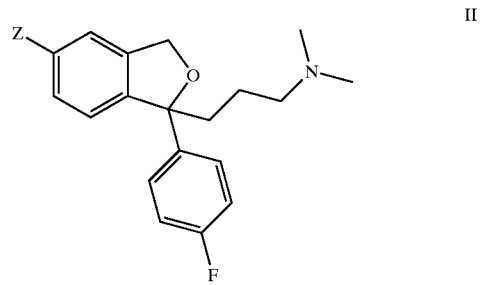

wherein Z is iodo, bromo, chloro or $CF_3-(CF_2)_n-SO_2-O-$ n being 0, 1, 2, 3, 4, 5, 6, 7 or 8, is subjected to a cyanide exchange reaction in which the group Z is exchanged with cyanide by reaction with a cyanide source; the resultant crude citalopram product is optionally subjected to some initial purification and the crude citalopram base is subsequently subjected to a film distillation process; the resulting citalopram product is then optionally further purified and worked up and isolated as the base or a pharmaceutically acceptable salt thereof.

14 Claims, No Drawings

OTHER PUBLICATIONS

U.S. Appl. No. 10/012,025, filed Nov. 6, 2001.
U.S. Appl. No. 10/012,054, filed Nov. 6, 2001.
U.S. Appl. No. 10/046,126, filed Jan. 8, 2002.
Levy, L.F., "4–Aminophthalide and Some Derivatives", *J. Chem. Soc.* pp. 867–870 (1931).
Tirouflet J., "Phtalide Substitutes en 5", *Bull. Soc. Sci. de Bretagne* 26:35–43 (1951).
Bigler, Allan et al., "Quantitative Structure–activity Relationships in a Series of Selective 5–HT uptake inhibitors,"*Eur. J. Med. Chem.* 3:289–295 (1997).
Forney L., "Reaction of Terephthalic Acid with Formaldehyde in Sulfur Trioxide Media," *J. Org. Chem.* 35:1695–1696 (1970).

Dordor et al., "Reaction of Oxazolines with Phosphorus Oxychloride," *Tetrahedron Letters* 24:1437–1440 (1983).

Barton et al., *Comprehensive Organic Chemistry. The Synthesis and Reactions of Organic Compounds*, vol. 2, pp. 1024–1025.

Neumüller, Dr. Otto–Albrecht, *Römpps Chemie–Lexikon* (*Achte, neubearbeitete und erweiterte Auflage*): 903–910; Stuttgart: Franchkh'sche Verlagshandlund (1981).

Bartholomé, Prof. Dr. E. et al., *Ullmanns Encyklopädie der technischen Chemie*:656–657; Weinheim/Bergstr.: Verlag Chemie.

R. Billet, *Sap. Technol.*, 2:183–191 (Oct. 1992).

PROCESS FOR THE PREPARATION OF PURE CITALOPRAM

This application is a continuation of PCT/DK01/00148, filed Mar. 7, 2001.

The present invention relates to a process for the manufacture of the well-known antidepressant drug citalopram, 1-[3-(dimethylamino)propyl]-1-(4-fluorophenyl)-1,3-dihydro-5-isobenzofuran-carbonitrile, in particular a process for preparing pure citalopram by cyanide exchange.

BACKGROUND OF THE INVENTION

Citalopram is a well-known antidepressant drug that has now been on the market for some years and has the following structure:

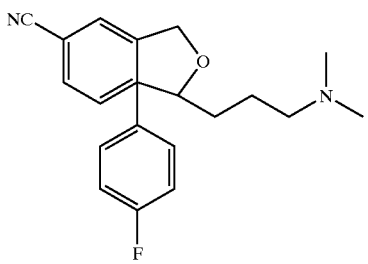

It is a selective, centrally acting serotonin (5-hydroxytryptamine; 5-HT) reuptake inhibitor, which has further been disclosed to show effects in the treatment of dementia and cerebrovascular disorders, cf. EP-A-474580.

Citalopram was first disclosed in DE 2,657,013, corresponding to U.S. Pat. No. 4,136,193. This patent publication i.a. outlines a process for preparation of citalopram from the corresponding 5-bromo-derivative by reaction with cuprous cyanide in a suitable solvent. Further processes for the preparation of citalopram by exchange of 5-halogen or $CF_3$—$(CF_2)_n$—$SO_2$—O—, n being 0–8, with cyano are disclosed in WO 0011926 and WO 0013648.

Other processes involve:
Conversion of a 5-amido or 5-ester group to a 5-cyano group (WO 9819513)
Conversion of a 5-amino group to a 5-cyano group (WO 9819512)
Conversion of a 5-formyl group to a 5-cyano group (WO 9900548)
Conversion of a 5-oxazolinyl or 5-thiazolinyl group to a 5-cyano group (WO 0023431)

It has turned out that it is difficult to manufacture citalopram in the required quality. The processes of DE 2,657,013, WO 0011926 and WO 0013648 comprising exchange of 5-halogen with cyano as described above have now been found to give some high molecular weight impurities including dimeric reaction products in unacceptable amounts. These impurities are difficult to remove by usual working up procedures leading to extensive and expensive purification processes.

Thus a process for the preparation of citalopram, in which impurities formed during the cyanide exchange reaction, i.e. the exchange of 5-halogen or the like with 5-cyano, are removed, is needed in order to obtain a commercially attractive manufacture of citalopram.

It has now been found that these high molecular reaction impurities may be removed by a film distillation process.

SUMMARY OF THE INVENTION

Accordingly, the present invention provides a novel process for the preparation of citalopram of formula

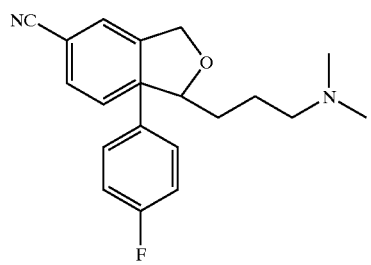

in which a compound of formula II

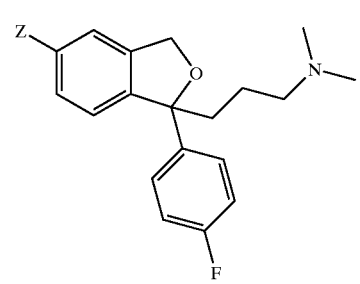

wherein Z is iodo, bromo, chloro or $CF_3$—$(CF_2)_n$—$SO_2$—O— n being 0, 1, 2, 3, 4, 5, 6, 7 or 8, is subjected to a cyanide exchange reaction in which the group Z is exchanged with cyanide by reaction with a cyanide source;

the resultant crude citalopram product is optionally subjected to some initial purification and the crude citalopram base is subsequently subjected to a film distillation process;

the resulting citalopram product is then optionally further purified and then worked up and isolated as the base or a pharmaceutically acceptable salt thereof.

In a further aspect, the invention relates to the above process in which the compound of formulaII is the S-enantiomer.

In yet another aspect, the present invention relates to an antidepressant pharmaceutical composition comprising citalopram manufactured by the process of the invention.

By the process of the invention, the high molecular impurities formed during the cyanide exchange reaction are removed from the crude citalopram product. The major parts of these high molecular impurities, which are formed during the cyanation reaction, are reaction products of formula III and

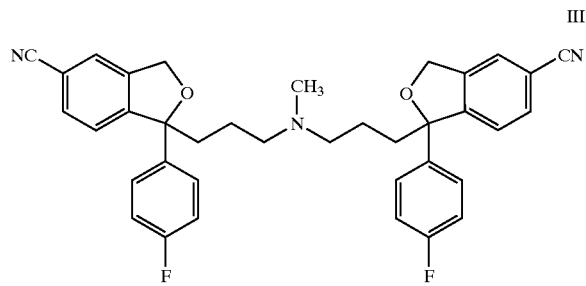

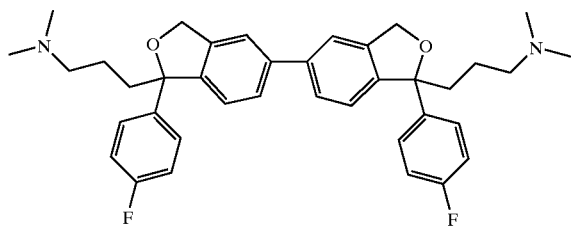

IV

In addition to the reaction products of formulas III and IV, other dimeric or polymeric impurities may e.g. be formed by reactions between descyano- and desmethyl-citalopram radicals formed during the cyanide exchange reaction. Furthermore, the reaction may be carried out under convenient conditions.

The cyanide exchange reaction may be carried out:
When Z is Br, by reaction with cuprous cyanide in a suitable solvent as described in U.S. Pat. No. 4,136,193,
When Z is iodo, bromo, chloro or $CF_3$—$(CF_2)_n$—$SO_2$—O— n being 0, 1, 2, 3, 4, 5, 6, 7 or 8, by reaction with a cyanide source in the presence a palladium catalyst and a catalytic amount of $Cu^+$ or $Zn^{2+}$ as described in WO0013648. Preferred cyanide sources are KCN, NaCN or $((R^a)_4N)CN$ where $(R^a)_4$ indicates four groups which may be the same or different and are selected from hydrogen and straight chain or branched alkyl. Alternatively the reaction may be carried out with $Zn(CN)_2$ in the presence of a palladium catalyst.

The palladium catalyst may be any suitable Pd(0) or Pd(II) containing catalyst, such as $Pd(PPh_3)_4$, $Pd_2(dba)_3$, $Pd(PPh_3)_2Cl_2$, etc. The catalysts, the reaction conditions, $Cu^+$ and $Zn^{++}$ sources, etc are further described in WO0013648.

The palladium catalysed process is in particular convenient when Z is Br.

When Z is Cl or Br, with a cyanide source in the presence of a nickel catalyst, as described in WO0011926. Preferred cyanide sources are KCN, NaCN or $((R^a)_4N)CN$ where $(R^a)_4$ indicates four groups which may be the same or different and are selected from hydrogen and straight chain or branched alkyl. The reaction may optionally be carried out in the presence of a catalytic amount of $Cu^+$ or $Zn^{2+}$.

The nickel catalyst may be any suitable Ni(0) or Ni(II) containing complex which acts as a catalyst, such as $Ni(PPh_3)_3$, (σ-aryl)-$Ni(PPh_3)_2Cl$, etc and it is preferably prepared in situ. The nickel catalysts and the reaction conditions are further described in WO0011926.

The nickel catalysed process is in particular convenient when Z is Cl.

The term alkyl refers to a branched or unbranched alkyl group, such as methyl, ethyl, 1-propyl, 2-propyl, 1-butyl, 2-butyl, 2-methyl-2-propyl, and 2-methyl-1-propyl.

The intermediate of formula II wherein Z is bromo or chloro may be prepared from bromo- and chlorophthalide, respectively, as described in DE 2,657,013 corresponding to U.S. Pat. No. 4,136,193. The compound wherein Z is iodo or Z is $CF_3$—$(CF_2)_n$—$SO_2$—O— may be prepared as described in WO 0013648. Preferably the intermediate wherein Z is Br is used.

Following to the cyanide exchange reaction and prior to distillation, the reaction mixture may be subjected to some initial purification, such as washing, extraction, crystallisation. Preferably the reaction mixture is washed with a mixture of an aqueous solvent and an organic solvent, e.g. a mixture of $H_2O$/ethylenediamine and toluene or of an aqueous EDTA-solution and toluene, in order to remove metal salt (originating from the cyanide source) and then the resulting crude citalopram is isolated as the base which is an oil.

The crude citalopram oil which is distilled may conveniently be dissolved in an appropriate solvent, i.e. an inert organic solvent, which is liquid at below 93° C. and is a gas at the evaporator temperature, in order to avoid that the distillation results in formation of a stony product. Preferably sulfolane is used.

The film distillation process may be any distillation process useful in industrial scale. The term "film distillation" designates a distillation process in which the evaporation of volatile substances from mixture to be distilled is performed by heating the mixture as a film. Convenient distillation processes are short path or thin film layer distillation.

Thin film layer distillation, which may also be called wiped film distillation, is a process in which the mixture to be distilled is applied to a surface in a heated apparatus as a thin film. Usually, the material is applied to the inner wall of a heated cylindrical evaporator by a rotor or wiper concentrically mounted in the apparatus. The distillate is usually condensed in an external condenser. Short path distillation is a film layer distillation process in which an internal condenser is placed with a short path of the vapours from the evaporation surface to the condenser.

According to the process of the invention, the film distillation process may be performed under the following conditions:
Feeding temperature higher than 93° C., preferably about 100° C.
Temperature of condensed distillate higher than 93° C., preferably about 100° C.
Distillation temperature of 200–330° C. at a pressure of 0.1–2.0 mmHg. The exact temperature depends on the pressure and may be determined by a person skilled in the art.

The crude citalopram base fed to the evaporator may be dissolved in an appropriate solvent, i.e. an inert organic solvent, which is fluid at below 93° C. and is a gas at the evaporator temperature.

In a particular preferred embodiment of the invention, a thin film layer distillation process is used. The thin film layer distillation is performed in a thin film layer evaporator which is a cylindrical apparatus with a double wall which provides for circulation of a heat transfer medium and with rotors or wipers placed on an axis concentrically in the cylinder. It has outlet for theremanence and for the distillate, respectively. The later outlet is through a condenser. The thin film layer distillation according to the invention may conveniently be performed under the following conditions:
The feeding temperature is higher than 93° C., preferably about 100° C.
The temperature of the condensed distillate is higher than 93° C., preferably about 120° C.
The distillation temperature, more specifically, the wiper or rotor temperature is 200–330° C. and the pressure is 0.1–2.0 mmHg, preferably 240–270° C. at a pressure of 0.6–0.8 mmHg
The rotor or wiper speed is 500–2000 rpm (rounds per minute) depending on the rotor and accordingly apparatus size. The smaller rotors the higher the speed. A convenient rotor speed is 1700–1800 rpm in a smaller apparatus or 700 rpm in an industrial scale thin film layer evaporator.

The crude citalopram base fed to the evaporator may be dissolved in an appropriate solvent, i.e. an inert organic solvent, which is liquid at below 93° C. and is a gas at the evaporator temperature. Preferably sulfolane is used.

Further purification of the citalopram product obtained by the distillation may if necessary be carried out by acid/base wash, crystallisation and recrystallisation of the citalopram base (cf. Dutch patent No 1016435) and/or crystallisation and recrystallisation of a pharmaceutically acceptable salt of citalopram.

The pharmaceutically acceptable salt of citalopram, such as the hydrobromide or hydrochloride, may be prepared by methods known in the art. So, the base may be reacted with either the calculated amount of acid in a water miscible solvent, such as acetone or ethanol, with subsequent isolation of the salt by concentration and cooling, or with an excess of the acid in a water immiscible solvent, such as ethylether, ethylacetate or dichloromethane, with the salt separating spontaneously. The hydrobromide or hydrochloride of citalopram obtained by the method of the invention has a very high purity, preferably more than 99.7% pure, most preferably more than 99.8% purity. Other salts of citalopram, e.g. the oxalate, may also be obtained in a very pure form by this process.

The pharmaceutical compositions of the invention may be administered in any suitable way and in any suitable form, for example orally in the form of tablets, capsules, powders or syrups, or parenterally in the form of usual sterile solutions for injection.

The pharmaceutical formulations of the invention may be prepared by conventional methods in the art. For example, tablets may be prepared by mixing the active ingredient with ordinary adjuvants and/or diluents and subsequently compressing the mixture in a conventional tabletting machine. Examples of adjuvants or diluents comprise: Corn starch, potato starch, talcum, magnesium stearate, gelatine, lactose, gums, and the like. Any other adjuvant or additive, colourings, aroma, preservatives etc. may be used provided that they are compatible with the active ingredients.

Solutions for injections may be prepared by solving the active ingredient and possible additives in a part of the solvent for injection, preferably sterile water, adjusting the solution to the desired volume, sterilising the solution and filling it in suitable ampoules or vials. Any suitable additive conventionally used in the art may be added, such as tonicity agents, preservatives, antioxidants, etc.

Finally, it has been found that the base may be formulated into very good and stable solid formulations with good release properties (cf. Dutch patent No 1016435).

The invention is further illustrated by the following examples.

EXAMPLE 1

Preparation of Crude Citalopram Base (5-cyano-1-(3-dimethylaminopropyl)-1-(4-fluorophenyl)phthalane)

Cu(I)CN (197 g, 2.2 mol) is added to a solution of 5-bromo-1-(4-fluorophenyl)-1-(3-methylaminopropyl) phthalane (720 g, 1.9 mol) in sulfolane (250 mL). After the reaction mixture has been heated to 150° C. for a period of 5 hours, sulfolane (500 mL) is added. The reaction mixture is cooled to 80° C. where ethylenediamine (aq, 50% w/v) is added. Toluene (2 L) is added and the phases are separated. The organic phase is further washed with EDTA (aq, 500 mL, 5% w/v) and water (2×500 mL). The volatile materials from the organic phase are removed in vacuo. 540 g of crude Citalopram base is isolated as an oil. Purity approx. 85% by HPLC (Peak area)

EXAMPLE 2

Purification of Crude Citalopram by Thin Film Distillation.

Crude citalopram base (5-cyano-1-(3-dimethylaminopropyl)-1-(4-fluorophenyl)phthalane)(20 kg, purity approx. 89% by HPLC (peak area) and sulfolane (4 L) is heated to approx. 100° C. The hot mixture is feeded to a thin film distillation apparatus (wiped film distillation) where the wiper temperature is 245° C. resulting in a pressure of about 0.7 mmHg. The temperature of the condensed distillate is kept at 120° C. to prevent crystallisation of the free base. The distillate contains crude citalopram (purity approx. 96% by HPLC (peak area)) and sulfolane.

EXAMPLE 3

Further Purification of the Distillate (Crude Citalopram Base) as Above by Crystallisation of the Free Base of Citalopram.

Distillate (4 kg) as above is dissolved in MeOH (12 L) at ambient temperature. Water is added until a "milky" colour of the mixture remains. This mixture is seeded with crystals of citalopram free base. The crystals are isolated by filtration after the temperature has been lowered to 10° C. for 2 hours. The crystallisation from MeOH/water as above is repeated. Two further re-crystallisations from n-heptane give Citalopram (2.3 Kg) free base in a purity of approx. 99.5% (HPLC: peak area)

What is claimed is:

1. A process for the preparation of citalopram of formula I

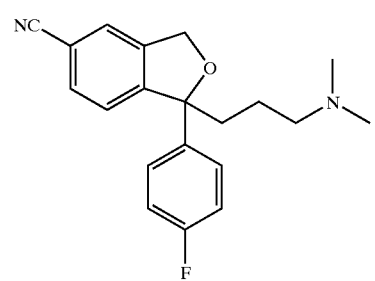

in which 1 a compound of formula II

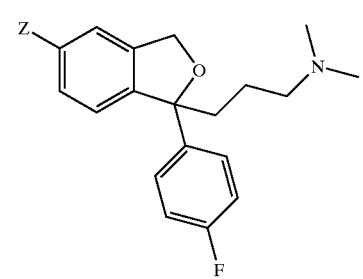

wherein Z is iodo, bromo, chloro or $CF_3$—$(CF_2)_n$—$SO_2$—O—; and n is 0, 1, 2, 3, 4, 5, 6, 7 or 8;

is subjected to a cyanide exchange reaction in which the group Z is exchanged with cyanide by reaction with a cyanide source;

the resultant crude citalopram product is optionally subjected to some initial purification and the crude citalopram base is subsequently subjected to a film distillation process, the resulting citalopram product is then optionally further purified, and worked up and 2 isolated as the product or a pharmaceutically acceptable salt thereof.

2. The process of claim 1, wherein the film distillation process is short path or thin film layer distillation.

3. The process of claim 2, wherein the film distillation process is thin film layer distillation.

4. The process of claim 1, wherein the crude citalopram base is dissolved in an appropriate solvent before it is subjected to film distillation.

5. The process of claim 1, wherein the distillation temperature is 200–330° C. and the pressure is 0.1–2.0 mmHg.

6. The process of claim 5, wherein the distillation temperature is 240–270° C. and the pressure is 0.6–0.8 mmHg.

7. The process of claim 1 wherein Z is bromo and the cyanide exchange reaction is carried out by reaction with cuprous cyanide in a suitable solvent.

8. The process of claim 1 wherein Z is iodo, bromo, chloro or $CF_3-(CF_2)_n-SO_2-O-$, n is 0, 1, 2, 3, 4, 5, 6, 7 or 8, and the cyanide exchange reaction is carried out by reaction with a cyanide source in the presence of a palladium catalyst and a catalytic amount of $Cu^+$ or $Zn^{2+}$.

9. The process of claim 1 wherein Z is iodo, bromo, chloro or $CF_3-(CF_2)_n-SO_2-O-$, n is 0, 1, 2, 3, 4, 5, 6, 7 or 8, and the cyanide exchange reaction is carried out with $Zn(CN)_2$ in the presence of a palladium catalyst.

10. The process of claim 8, wherein Z is bromo.

11. The process of claim 1, wherein Z is chloro or bromo and the cyanide exchange reaction is carried out with a cyanide source in the presence of a nickel catalyst.

12. The process of claim 8, wherein Z is chloro.

13. The process of claim 4 wherein the solvent is sulfolane.

14. The process of claim 11 which occurs in the presence of a catalytic amount of $Cu^+$ or $Zn^{2+}$.

* * * * *